United States Patent [19]

Biber et al.

[11] Patent Number: 5,694,815
[45] Date of Patent: Dec. 9, 1997

[54] OPTICAL THERAPEUTIC AND/OR DIAGNOSTIC INSTRUMENT WHICH CAN BE POSITIONED ABOUT AT LEAST ONE SPATIAL AXIS UTILIZING A HANDLE ASSEMBLY

[75] Inventors: Klaus Biber, Aalen; Fritz Zimmermann, Essingen, both of Germany

[73] Assignee: Carl-Zeiss-Stiftung, Heidenheim, Germany

[21] Appl. No.: 516,312

[22] Filed: Aug. 17, 1995

[30] Foreign Application Priority Data

Aug. 26, 1994 [DE] Germany ............... 44 30 295.9

[51] Int. Cl.⁶ ............... G05G 1/12; G05G 5/06
[52] U.S. Cl. ............... 74/528; 74/548; 74/553; 403/328; 16/DIG. 24; 16/114 R
[58] Field of Search ............... 74/528, 553, 543, 74/548; 403/327, 328; 16/DIG. 24, 114 R; 359/368, 383, 384, 372

[56] References Cited

U.S. PATENT DOCUMENTS

| | | | |
|---|---|---|---|
| 369,159 | 8/1887 | Burns | 403/328 X |
| 1,208,839 | 12/1916 | Salfisberg | 74/548 |
| 1,797,776 | 3/1931 | Jacobi | 403/328 X |
| 1,992,901 | 2/1935 | McIntosh | 74/528 |
| 4,684,088 | 8/1987 | Heller . | |
| 4,742,947 | 5/1988 | Coffman et al. | 359/383 X |
| 5,301,570 | 4/1994 | Li | 74/528 X |

FOREIGN PATENT DOCUMENTS

| | | | |
|---|---|---|---|
| 4311467 | 2/1994 | Germany . | |
| 56-158318 | 12/1981 | Japan | 359/368 |

*Primary Examiner*—Rodney H. Bonck
*Assistant Examiner*—Mary Ann Battista
*Attorney, Agent, or Firm*—Walter Ottesen

[57] ABSTRACT

The handle of the handle assembly can be detachably mounted in at least two different orientations relative to a defined apparatus axis. Furthermore, actuating elements of the particular instrument can be reached without difficulty via a suitable cutout in the handle without it being necessary for the operator to significantly change the manual hold on the handle. The handle assembly is especially advantageous on a surgical microscope.

13 Claims, 3 Drawing Sheets

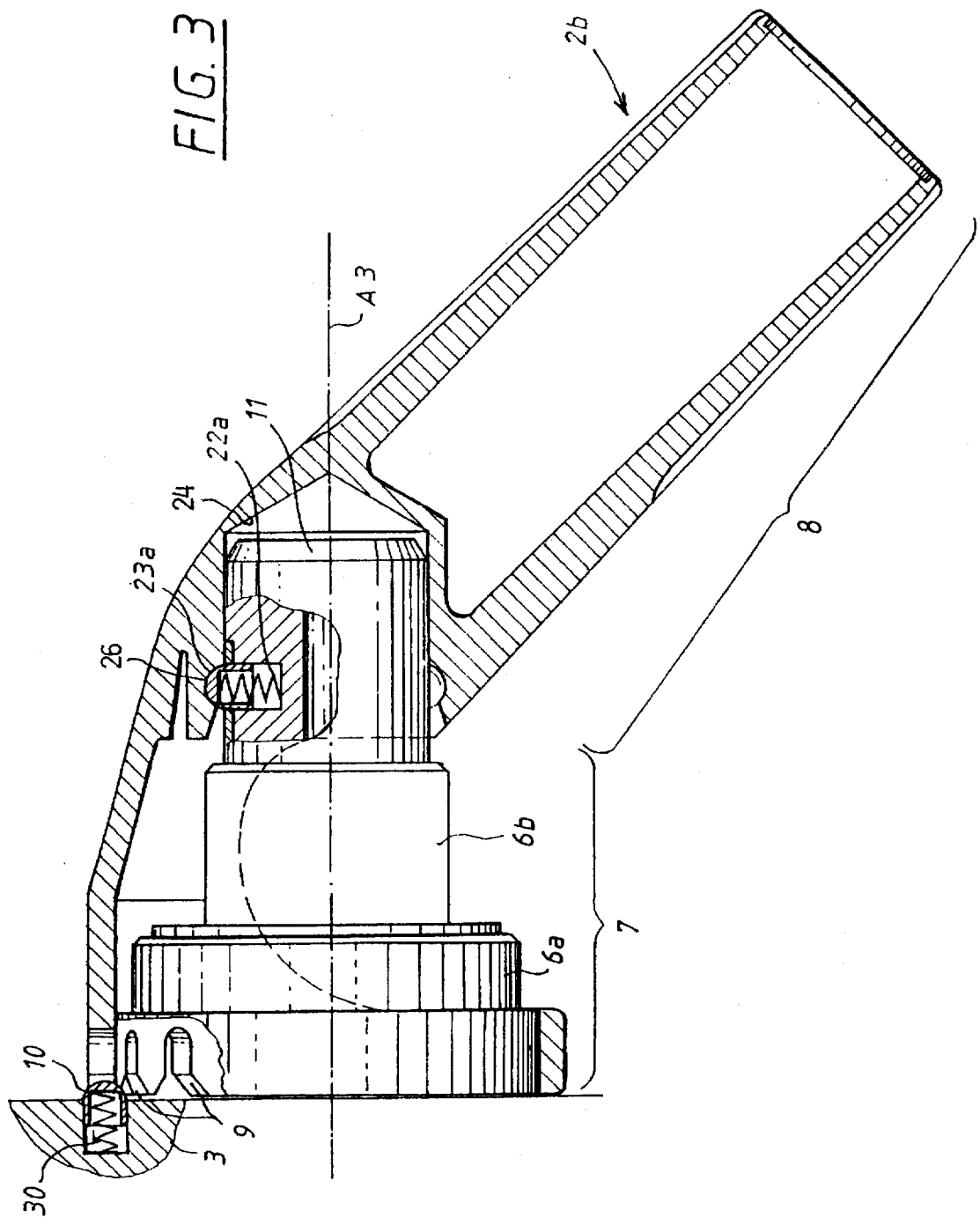

OPTICAL THERAPEUTIC AND/OR DIAGNOSTIC INSTRUMENT WHICH CAN BE POSITIONED ABOUT AT LEAST ONE SPATIAL AXIS UTILIZING A HANDLE ASSEMBLY

FIELD OF THE INVENTION

The invention relates to a handle assembly for an optical therapeutic and/or diagnostic instrument which can be positioned about several spatial axes. One or more such handles are especially suitable for mounting on a surgical microscope.

BACKGROUND OF THE INVENTION

Surgical microscopes are most often mounted on floor stands or ceiling stands. These stands, as a rule, permit the surgical microscope to be freely positioned in at least two spatial degrees of freedom or, more specifically, about several defined spatial axes. The stands are provided with known weight compensating mechanisms to make spatial positioning substantially free of force.

The surgeon during surgery is then faced with the problem to position the surgical microscope definitively in space in order to assume the optimal viewing position relative to the patient. For this purpose, the surgical microscope usually has at least one handle which is mounted laterally on the housing of the surgical microscope. Two such handles are preferably provided. The surgical microscope can assume a plurality of possible tilt positions because of the free positionability in space. For this reason, the handles mounted on the surgical microscope often do not have those positions for the operator which are ergonomically optimal.

Furthermore, when positioning or after the surgical microscope is positioned, operator-controlled elements must be manually actuated on the surgical microscope such as the focusing or the adjustment of magnification. In this context, it should not be necessary for the surgeon to move from one handle to another during positioning; rather, the particular actuating elements for these functions should be accessible during spatial positioning of the surgical microscope without having to change the grip on the handle.

For this purpose, it is, for example, known from German published patent application 4,311,467 that suitable buttons can be integrated directly into the handles in order to avoid changing from one handle to the next. As already mentioned, there are however positions of the surgical microscope in space in which an actuation of these elements is no longer possible in a manner which is ergonomically optimal for the arrangement of the handles described in said German published patent application.

Problems similar to those described initially result, however, not only for the above-mentioned surgical microscopes, but also for a wide selection of other optical therapeutic and/or diagnostic instruments which can be positioned about several spatial axes.

SUMMARY OF THE INVENTION

In view of the foregoing, it is an object of the invention to provide a handle assembly for an optical therapeutic and/or diagnostic instrument which can be positioned about several spatial axes. It is a further object of the invention to provide such a handle wherein the above-mentioned disadvantages are avoided and a manipulation in all realizable positions of the particular instrument is always guaranteed with this manipulation being as ergonomic as possible.

The handle assembly of the invention is for an optical therapeutic and/or diagnostic instrument which can be positioned about at least one spatial axis. The handle assembly includes: a mount attached to the instrument and the mount defining a longitudinal axis; a handle seated on the mount so as to be rotatable about the longitudinal axis; the handle and the instrument conjointly defining an interface; and, an indexing device located at the interface for releasably holding the handle in at least two different positions relative to the longitudinal axis.

Thus, according to the invention, the handle can be releasably mounted in various orientations relative to the axis of the apparatus. For this reason, it is ensured that for any desired spatial positioning of the optical therapeutic and/or diagnostic instrument, also an optimal ergonomic manipulation results for the operator. It is especially advantageous that a series of different possible detent positions are provided for the handle on the particular instrument in order to make possible an individual manipulation of the instrument for each user.

At least one such handle according to the invention is especially suitable for spatially positioning a surgical microscope. However, this handle can be applied for similar tasks even on the most varied of optical therapeutic and/or diagnostic instruments or the like.

Furthermore, the handle assembly according to the invention makes it possible for an operator to actuate an actuating element which is mounted between the handle and the particular instrument. This is achieved via the suitable geometric dimensioning of the handle. For this purpose, a control knob is, for example, suitable as an actuating element. With the control knob, specific functions of the instrument can be activated manually or via a motor. The actuation of this element is even then relatively simple when a surgical microscope must be covered during the surgery for reasons of sterility.

BRIEF DESCRIPTION OF THE DRAWINGS

The invention will now be described with reference to the drawings wherein:

FIG. 3 is a section view of the handle of FIG. 1 and the actuating element mounted therebelow;

DESCRIPTION OF THE PREFERRED EMBODIMENTS OF THE INVENTION

Figure 1:
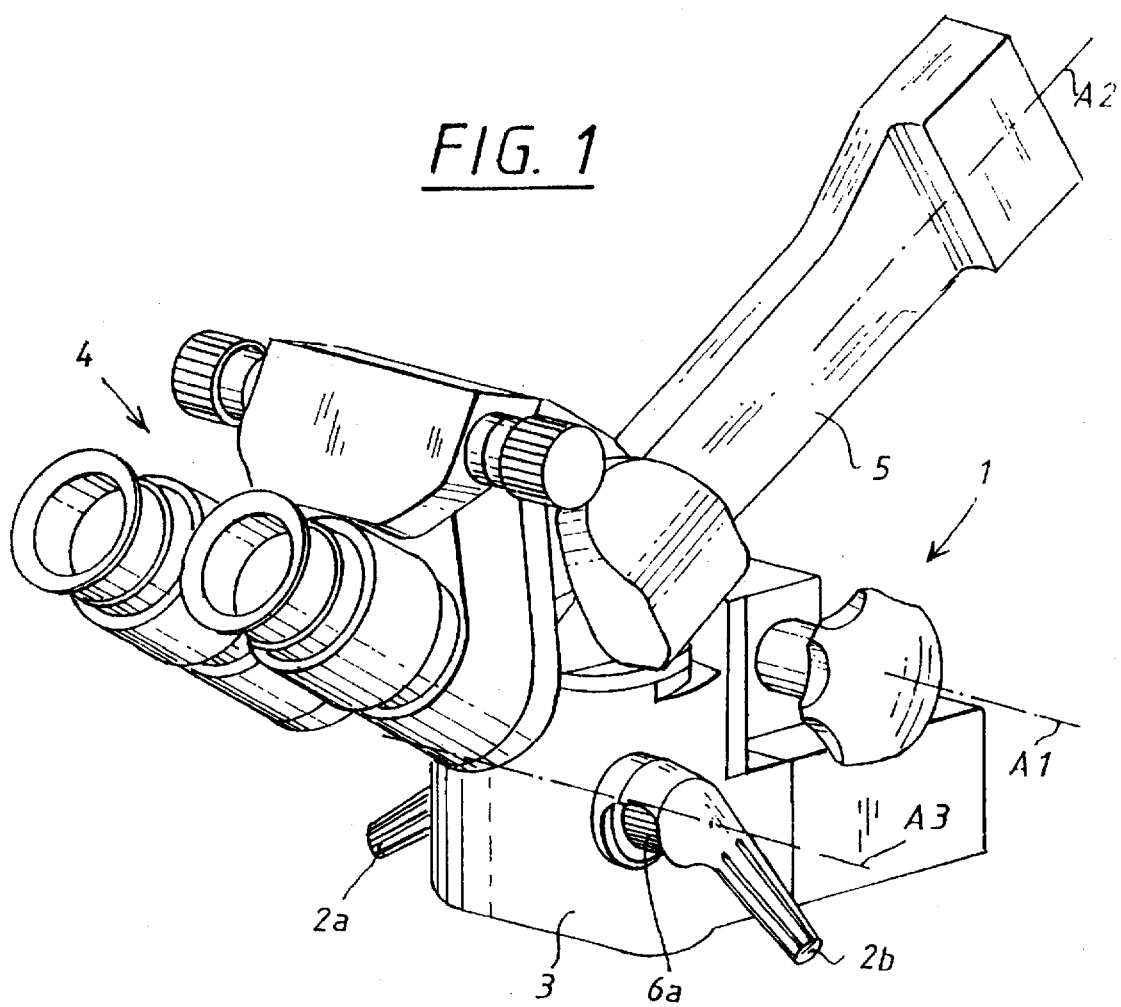
FIG. 1 is a perspective view of a surgical microscope mounted on a carrier system with the microscope having two handles according to the invention attached thereto.

FIG. 1 shows a perspective view of a surgical microscope 1 mounted to a carrier system (not shown). Two handles (2a, 2b) according to the invention are mounted on the surgical microscope 1. It is also possible to mount only one of the two handles (2a or 2b) on the surgical microscope 1 when, for example, the mounting of a second handle (2a or 2b) is not possible because of laterally mounted documentation devices or the like.

The surgical microscope 1 shown has a configuration which is essentially known per se. The optical system having main objective, magnification changer, barrel lenses and the like is mounted in the housing 3 of the surgical microscope. A known pivotable binocular tube 4 for the viewer is provided above the housing 3 of the surgical microscope 1. Furthermore, the surgical microscope 1 includes an illumination device known per se.

The surgical microscope 1 is connected to the carrier system (not shown) via a connecting element 5. Floor-mounted or ceiling-mounted stands are suitable carrier systems which make possible a free positioning of the surgical microscope in several spatial degrees of freedom. In this connection, reference may be made, for example, to U.S. Pat. No. 4,684,088. The embodiment of the surgical microscope shown is mounted on the carrier system and can be tilted or pivoted about two spatial axes (A1, A2). Depending upon the conditions of use and the geometry of the surgical microscope and/or carrier system utilized, the surgical microscope can also be positioned about only one axis or along one axis or about more than two axes.

Each one of the handles (2a, 2b) is detachably mounted on a side of the housing 3 of the surgical microscope 1. The detachable mounting of the handles (2a, 2b) is possible in several orientations relative to a defined apparatus axis A3 of the surgical microscope. In the embodiment shown, this apparatus axis A3 is defined by the connecting line of the center points of the mounting surfaces of the handles (2a, 2b) on the housing 3 and is thereby orientated parallel to the pivot axis A1 of the surgical microscope 1.

This apparatus axis can, however, be orientated relative to the instrument as desired. What is essential is only the detachable attachment of the handle in at least two positions relative to an instrument fixed reference normal.

FIG. 1 shows the basic assembly of the handles (2a, 2b) according to the invention which comprise an attachment part and a handle part. In the embodiment shown, the attachment part has suitable cutouts by which the operator can simultaneously operate one or more of the actuating elements 6a with the hands on the handles (2a, 2b). The actuating elements (6a, 6b) enable, for example, specific functions of the surgical microscope 1 to be activated or controlled. In the embodiment of FIG. 1, the magnification adjustment and the focusing are controlled via the actuating elements (6a, 6b) and, for this purpose, corresponding motorized drives are provided in the housing 3 of the surgical microscope 1.

Actuating elements can also be provided at this location which can make possible a manual change of specific instrument settings.

Figure 2A:
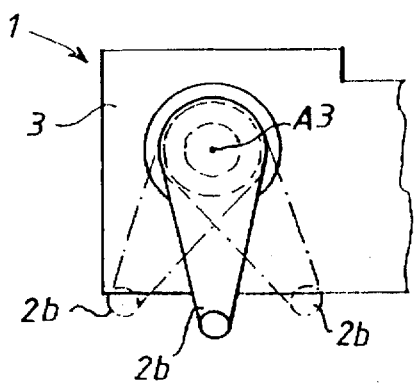
FIG. 2A is a detail view of the surgical microscope of FIG. 1 showing a front view of a handle assembly according to the invention with the handle shown in several possible detent positions.

The detail side elevation view of FIG. 2A shows the surgical microscope 1 of FIG. 1 with one of the two handles 2b according to the invention. FIG. 2A shows the base position (solid line) of the handle 2b as well as two further possible positions (phantom outline) thereof relative to an apparatus axis A3 of the surgical microscope 1. In the embodiment shown, several latch locations are provided for the handle 2b which correspond to different positions of the handle 2b relative to the apparatus axis A3. The second handle 2a on the opposite side of the surgical microscope 1 is arranged completely analog to the handle 2b.

Figure 2B:
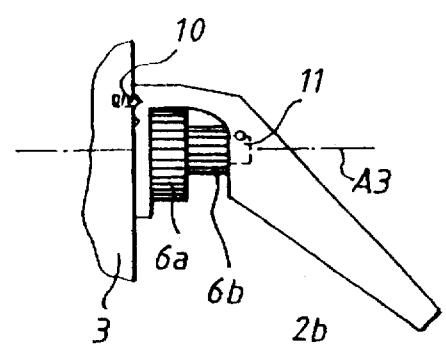
FIG. 2B is a detail view of the surgical microscope of FIG. 1 showing a side elevation view of one of the two handle assemblies and an actuating element mounted therebelow with the actuating element being in the form of a double rotary knob.

A detail front elevation view of the handle 2b mounted on the surgical microscope of FIG. 2A is shown in FIG. 2B including two actuating elements (6a, 6b) disposed below the handle. The actuating elements (6a, 6b) are configured as double rotary knobs which drive the motorized drives for varying the magnification and for adjusting focusing of the surgical microscope. Furthermore, FIG. 2B also clearly shows how the operator, with the aid of the thumb, can actuate the rotary knobs (6a, 6b) without releasing the grasp from the handle 2b or without having to grasp another handle.

The apparatus axis A3 is likewise shown in FIG. 2B and it is relative to this axis that the handle 2b can be detachably mounted in at least two defined positions on the housing 3 of the surgical microscope.

The detachable arrangement of the handle 2b of the invention on the surgical microscope is provided in the embodiment shown via a latch connection with a mounting element 11 arranged coaxially to the actuating elements (6a, 6b). The detent element engages form-tight in a corresponding opposite-lying cutout of the handle 2b. For ensuring the desired reproducible position of the handle, a latch device is provided between the handle 2b and the housing 3 of the surgical microscope. This latch device includes at least one detent element 10 which engages form-tight in a corresponding recess 9 of the handle 2b. The detent element 10 is resiliently biased by a pressure spring and is arranged on the surgical microscope. A row of recesses is, in turn, provided on the handle 2b. These recesses are arranged in rotational symmetry about the apparatus axis A3. The detent element 10 of the latching device latches into any one of a plurality of recesses for various positions of the handle 2b.

Further details of the handle of the invention are described with respect to FIG. 3. FIG. 3 shows a section view of the handle of FIGS. 1, 2A and 2B together with the actuating elements arranged therebelow.

In the embodiment shown, the handle 2b of the invention has essentially a two-part assembly. For this purpose, an attachment part 7 is provided which faces toward the particular instrument on which the handle 2b is to be mounted. Furthermore, a handle part 8 of the handle 2b facing away from the instrument is provided which the operator grasps and via which the actual positioning of the instrument used takes place. Both parts of the handle 2b can, in principle, also be manufactured as a single part.

A material suitable for the handle is a plastic material manufactured by BASF of Germany under the product designation PES GF Ultrason E 1010 G4. It is preferable to use a material here which permits the handle to be sterilized.

The attachment part 7 of the handle 2b of the embodiment shown is configured to be at least partially rotationally symmetric with respect to the apparatus axis A3; whereas, the handle part 8 of the handle 2b is mounted with its longitudinal axis at a defined angle to the apparatus axis A3. Depending upon the desired latch location of the handle 2b, various orientations of the handle part 8 relative to the apparatus axis A3 are possible; that is, an individual adjustment of the handle 2b relative to the instrument is possible.

As an alternative to the embodiment of the handle part described, it is, in principle, also possible to make the angle between the symmetry axes of the attachment part and the handle part variable or even to provide a series of different embodiments of this kind of the handle having different angles.

Furthermore, in lieu of the two-part assembly described, a one-part handle can be used which is detachably arranged at a specific angle relative to the apparatus axis in at least two positions relative to the instrument.

The handle 2b according to the invention is mounted on the housing 3 of the particular instrument in an advantageous embodiment via a latch connection. The latch connection includes a mounting element 11 mounted on the rotary knobs (6a, 6b). The handle 2b can then be fixed on the mounting element 11. For this purpose, the handle 2b includes a corresponding opposite-lying recess 24. In the embodiment shown, the latch connection further includes detent pins 23a which are radially mounted in the mounting element 11 and which are resiliently biased by springs 22a. The detent pins 23a engage in an annular slot 26 in the interior of handle 2b.

As an alternative to the latch connection, suitable screw connections or pin-and-socket connections can be utilized between the handle and the particular housing of the instrument in order to ensure the detachable mounting of the handle of the invention on the instrument.

In addition to the latch connection described, the attachment part 7 of the handle of the invention further includes a latching device. This latching device comprises, on the one hand, cutouts 9 on the handle 2b of which only three cutouts can be seen in FIG. 3. The cutouts 9 are arranged rotationally-symmetrically on the handle 2b. At least one further detent element engages form-tight in the cutouts 9 of the latching device. The detent pin 10 is oppositely dimensioned to correspond to the cutouts 9 and is mounted on the housing 3 of the particular instrument. In the embodiment shown, the detent pin 10 is resiliently biased by a spring 30 and pressed outwardly. The cutouts 9 in the handle 2b are arranged rotationally-symmetrical about the apparatus axis A3 on the particular instrument so that the detachable arrangement of the handle 2b is provided in at least three positions relative to the instrument.

The latching device described ensures the reproducible and detachable attachment of the handle in the desired relative position. The annular slot 26 referred to above facilitates rotation of the handle 2b about axis A3 between the different angular positions defined conjointly by recesses 9 and resiliently biased detent element 10.

As an alternative to the latching device shown, it is also possible, if required, to provide a locking screw on the handle as the holding element which engages in corresponding recesses of the handle in order to guarantee reproducible relative positions of the handle to the instrument.

The attachment part 7 of the handle 2b of the invention is configured in the embodiment shown as a part cylinder so that an actuation of the actuating element (6a, 6b) is possible at any time via the cutout provided on the handle 2b without it being necessary to release the hand from the handle 2b. The actuating elements (6a, 6b) are mounted below the attachment part 7. In the embodiment of FIG. 3, two rotary knobs (6a, 6b) are provided as actuating elements. The rotary knobs (6a, 6b) are mounted coaxially with respect to each other between the housing 3 of the surgical microscope and the handle 2b. Switching elements integrated into the rotating rotary knobs are actuated by tapping the knobs in a defined direction. The switching elements activate specific motorized functions of the instrument.

Figure 5:
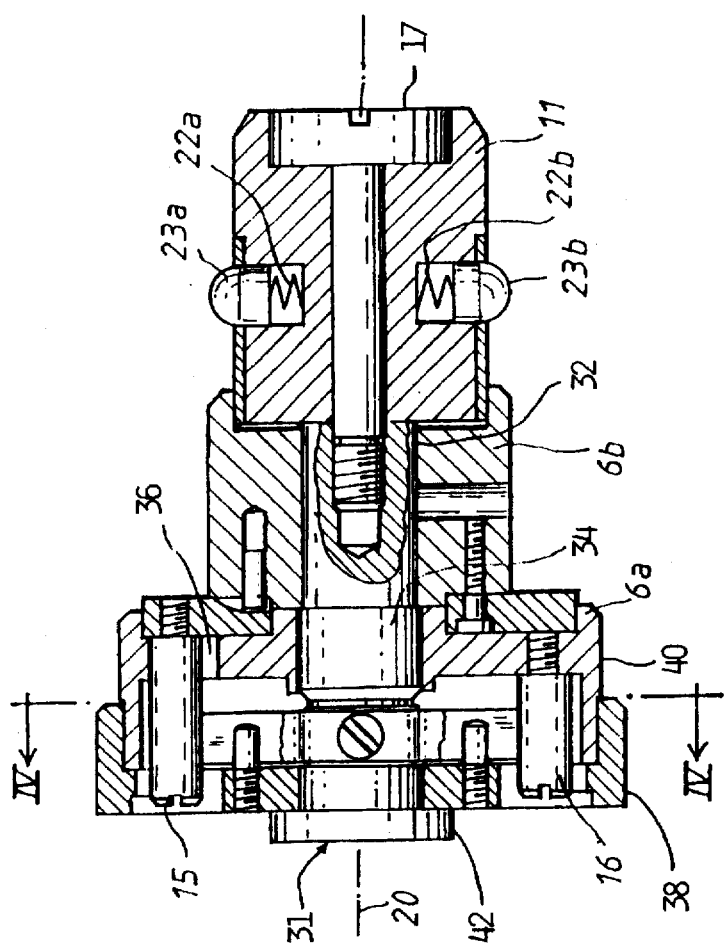
Figure 4:
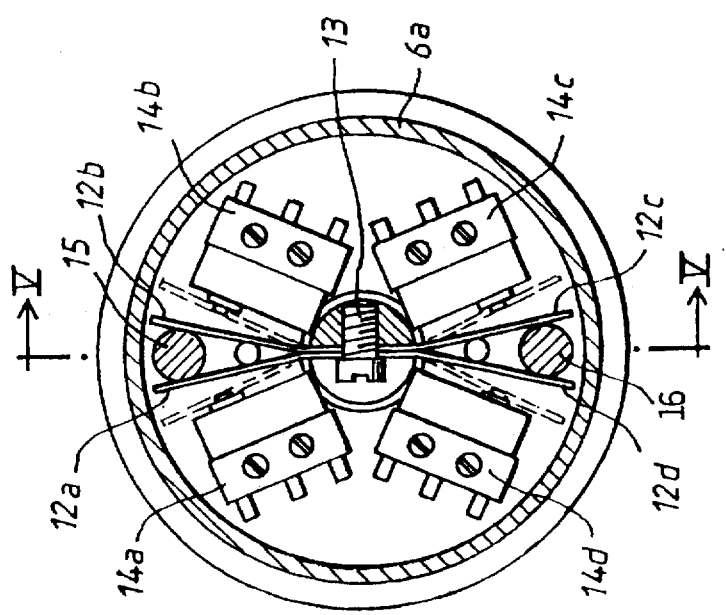
FIG. 4 is a plan view taken along line IV—IV of FIG. 5 through an actuating element configured as a double rotary knob above which the handle according to the invention is mounted; and, FIG. 5 is a side elevation section view of the rotary know of FIG. 4 taken along line V—V thereof.

FIGS. 4 and 5 show the actuating elements utilized in combination with the handle of the invention. Referring to FIGS. 4 and 5, double rotary knobs (6a, 6b) are provided in coaxial relationship to each other as explained above. The double rotary knobs (6a, 6b) facilitate the activation via electric motors of specific instrument functions such as focusing and defocusing, adjusting magnification and the like.

FIG. 4 shows the switching elements integrated into the lower of one of the two rotary knobs (6a, 6b). The switching elements are configured here as a total of four microswitches (14a, 14b, 14c, 14d) and four leaf springs (12a, 12b, 12c, 12d) are provided to resiliently bias corresponding ones of the microswitches (14a, 14b, 14c, 14d). Two of the microswitches are assigned to rotary knob 6a and the remaining two are assigned to rotary knob 6b. When the particular rotary knob (6a or 6b) is rotated, the microswitches assigned thereto are actuated via the leaf springs corresponding thereto. Thus, in the embodiment shown, the two lower microswitches (14c, 14d) are assigned to the lower or inner rotary knob 6a and activate the motorized focusing. On the other hand, the two upper microswitches (14a, 14b) are assigned to the upper or outer one of the two rotary knobs and operate to activate motorized variation of the magnification.

Accordingly, when a force is applied to the leaf springs (12a to 12d), electrical control signals are initiated via microswitches (14a to 14d) for activating specific motorized functions of the surgical microscope. The corresponding motorized functions are correspondingly activated for a length of time depending upon the duration of activation.

The leaf springs (12a to 12d) are deflected by the entraining pin (15 or 16) connected to a corresponding rotary knob (6a or 6b) when the rotary knob (6a or 6b) is actuated. In this way, and in dependence upon the direction of the resulting movement of the rotary knob (6a or 6b), a focusing or a defocusing of the surgical microscope, for example, takes place. Reference numeral 36 identifies an annular slot formed in rotary knob 6a so as to permit pin 15 to move along a circular arc without being hindered by rotary knob 6a.

FIG. 5 shows a further section view through the actuating elements configured as double rotary knobs (6a, 6b). A shaft 31 includes as an integral element the following: shaft segment 32, shaft segment 34 and flange 42. The two rotary knobs (6a, 6b) are rotatably journalled on shaft segments 34 and 32, respectively, for rotation about the common rotational axis 20. The rotary knobs are rotatable one relative to the other and are connected to corresponding entraining pins (15, 16) via which a force is applied to the microswitches via the leaf springs as described above. The entire mechanical and electrical assembly including the shaft 31 is supported on a disc-shaped holder 38 which is attached to the housing of the surgical microscope using threaded fasteners (not shown). The shaft 31 is fixedly held in the holder 38 and the flange 42 is seated in a recess (not shown) of the surgical housing.

FIG. 5 also shows the mounting element 11 of the latching connection with the detent pins (23a, 23b). The mounting element 11 is attached to the shaft segment 32 by means of a screw 17 and the detent pins (23a, 23b) are resiliently biased by the springs (22a, 22b), respectively. The detent pins (23a, 23b) engage in the opposite annular slot 26 of the handle 2b as shown in FIG. 3.

In addition to the latchability of the handle 2b at various angular positions relative to the axis A3, it is a very significant further advantage of the invention that the entire handle 2b can be simply removed from the holding element 11 by applying an adequate pulling force in the direction of axis A3 which causes the detent pins 23a, 23b) to compress the respective springs (22a, 22b) and slip out of the slot 26. For this reason, the operator can quickly and simply remove the handle 2b from the surgical microscope.

As already mentioned, the described actuating elements show only one possible embodiment, that is, a whole series of alternate actuating elements can be used in combination with the handle of the invention.

It is understood that the foregoing description is that of the preferred embodiments of the invention and that various changes and modifications may be made thereto without departing from the spirit and scope of the invention as defined in the appended claims.

What is claimed is:

1. In an optical therapeutic or diagnostic instrument which can be positioned about at least one spatial axis utilizing a handle assembly, the handle assembly comprising:

a mount attached to said instrument and said mount defining a longitudinal axis;

a handle seated on said mount so as to be rotatable about said longitudinal axis;

said handle and said instrument conjointly defining an interface;

an indexing device located at said interface for releasably holding said handle in at least one of two different positions relative to said longitudinal axis;

said handle having a cutout formed therein;

an actuating element for an operator and said actuating element being mounted between said instrument and said handle; and, said cutout being adapted to permit the operator to adjust said actuating element while holding said handle and without significantly changing the grip on the handle.

2. The handle assembly of claim 1, said actuating element being at least one rotary knob.

3. The handle assembly of claim 1, said actuating element including two rotary knobs mounted coaxially relative to each other.

4. The handle assembly of claim 3, each one of said rotary knobs including at least one switching element for generating a control signal when said rotary knob is actuated; and, said control signal activating a particular motorized function of said instrument.

5. The handle assembly of claim 4, wherein said control signal serves to change magnification.

6. An optical therapeutic or diagnostic instrument assembly which can be positioned about at least one spatial axis, the instrument assembly comprising:

an optical or diagnostic instrument;

a handle assembly which includes:

a mount attached to said instrument and said mount defining a longitudinal axis;

a handle seated on said mount so as to be rotatable about said longitudinal axis;

said handle and said instrument conjointly defining an interface; and, an indexing device located at said interface for releasably holding said handle in one of at least two different positions relative to said longitudinal axis;

said handle having a cutout formed therein;

an actuating element for an operator and said actuating element being mounted between said instrument and said handle; and, said cutout being adapted to permit the operator to adjust said actuating element while holding said handle and without significantly changing the grip on the handle.

7. A surgical microscope assembly adapted to be mounted on a carrier system which can be freely positioned about at least one spatial axis, the surgical microscope assembly comprising:

a surgical microscope;

a handle assembly which includes:

a mount attached to said surgical microscope and said mount defining a longitudinal axis;

a handle seated on said mount so as to be rotatable about said longitudinal axis so as to permit changing said handle in position relative to said surgical microscope;

said handle and said surgical microscope conjointly defining an interface;

an indexing device located at said interface for releasably holding said handle in one of at least two different index positions relative to said longitudinal axis and said surgical microscope with a holding force sufficient to permit an operator to move said surgical microscope about said at least one spatial axis in at least two positioning directions without dislodging said handle from a selected one of said index positions;

said indexing device being a latching device for releasably latching said handle in said at least two different index positions about said longitudinal axis relative to said surgical microscope; and, said latching device being configured so as to make said index positions reproducible each time said handle is adjusted.

8. The surgical microscope assembly of claim 7, said latching device including: a detent mounted on said surgical microscope and facing toward said handle; and, a plurality of symmetrically-shaped cutouts formed in said handle for corresponding ones of said positions wherein said detent engages one of said symmetrically-shaped cutouts to provide an interlock therewith.

9. The surgical microscope assembly of claim 7, said latching device including at least one detent mounted on one of said surgical microscope and said handle; a plurality of cutouts formed on the other one of said surgical microscope and said handle; and, said cutouts corresponding to said index positions, respectively.

10. The surgical microscope assembly of claim 7, said mount including a holder coaxial with said longitudinal axis for engaging said handle when said handle is mounted on said surgical microscope; said mount and said handle conjointly defining a second interface; and, a holding device located at said second interface for releasably holding said handle on said mount.

11. The surgical microscope assembly of claim 10, said holding device including a detent element arranged on said holder; and, said handle including a recess formed therein for releasably engaging said detent element when said handle engages said holder.

12. The surgical microscope assembly of claim 11, said handle comprising an attachment part facing toward said surgical microscope and a grip part facing away from said surgical microscope; and, said attachment part being arranged relative to said grip part at a predetermined angle.

13. The surgical microscope assembly of claim 12, said attachment part being at least partially rotationally symmetric to said longitudinal axis and being locatable in at least one of said at least two index positions relative to said longitudinal axis; and, said grip part being at a predetermined angle relative to said longitudinal axis.

* * * * *